(12) United States Patent
White et al.

(10) Patent No.: US 8,216,409 B2
(45) Date of Patent: Jul. 10, 2012

(54) METHODS FOR MAKING A HOUSINGLESS HOLLOW FIBER FILTRATION APPARATUS

(75) Inventors: James Mitchell White, Niskayuna, NY (US); Nichole Lea Wood, Niskayuna, NY (US); Weston Blaine Griffin, Niskayuna, NY (US); Ryan Austin Hutchinson, Albany, NY (US); Owen Scott Quirion, Clifton Park, NY (US); Philip Alexander Shoemaker, Scotia, NY (US); Eric Douglas Williams, Duanesburg, NY (US)

(73) Assignee: General Electric Company, Niskayuna, NY (US)

( * ) Notice: Subject to any disclaimer, the term of this patent is extended or adjusted under 35 U.S.C. 154(b) by 398 days.

(21) Appl. No.: 12/635,231

(22) Filed: Dec. 10, 2009

(65) Prior Publication Data

US 2011/0139345 A1 Jun. 16, 2011

(51) Int. Cl.
*B65H 81/00* (2006.01)

(52) U.S. Cl. ........ 156/174; 156/166; 156/173; 156/175; 156/309.6

(58) Field of Classification Search .......... 156/166, 156/173, 174, 175, 308.2, 309.6
See application file for complete search history.

(56) References Cited

U.S. PATENT DOCUMENTS

| | | | | | |
|---|---|---|---|---|---|
| 3,442,002 | A | * | 5/1969 | Geary, Jr et al. | 29/450 |
| 4,038,190 | A | * | 7/1977 | Baudet et al. | 210/321.81 |
| 4,190,411 | A | * | 2/1980 | Fujimoto | 425/434 |
| 4,231,871 | A | * | 11/1980 | Lipps et al. | 210/87 |
| 4,276,175 | A | * | 6/1981 | Bower | 210/636 |
| 4,329,229 | A | * | 5/1982 | Bodnar et al. | 210/321.89 |
| 4,689,191 | A | * | 8/1987 | Beck et al. | 264/573 |
| 5,282,966 | A | | 2/1994 | Walker | |
| 5,445,771 | A | * | 8/1995 | Degen | 264/488 |
| 5,556,591 | A | | 9/1996 | Jallerat et al. | |
| 5,695,489 | A | | 12/1997 | Japuntich | |
| 5,792,133 | A | | 8/1998 | Rochat | |
| 7,429,325 | B2 | | 9/2008 | Ingvarsson | |

FOREIGN PATENT DOCUMENTS

| | | | |
|---|---|---|---|
| EP | 0752904 B1 | | 8/1998 |
| JP | 2000-271212 A | * | 10/2000 |
| WO | WO9312866 A1 | | 7/1993 |
| WO | WO-96/04067 A1 | * | 2/1996 |
| WO | WO-96/04068 A1 | * | 2/1996 |
| WO | WO9604068 A1 | | 2/1996 |
| WO | WO-2008/026079 A2 | * | 3/2008 |
| WO | WO2008026079 A2 | | 3/2008 |

OTHER PUBLICATIONS

PCT International Search Report dated Jan. 26, 2011 and Written Opinion.

* cited by examiner

*Primary Examiner* — Jeff Aftergut
(74) *Attorney, Agent, or Firm* — Eileen B. Gallagher

(57) ABSTRACT

The invention provides a method of manufacturing a housingless hollow fiber filtration apparatus using batch, continuous, and semi-continuous processes. Also provided is manufacturing methods to increase rigidity of the apparatus.

10 Claims, 10 Drawing Sheets

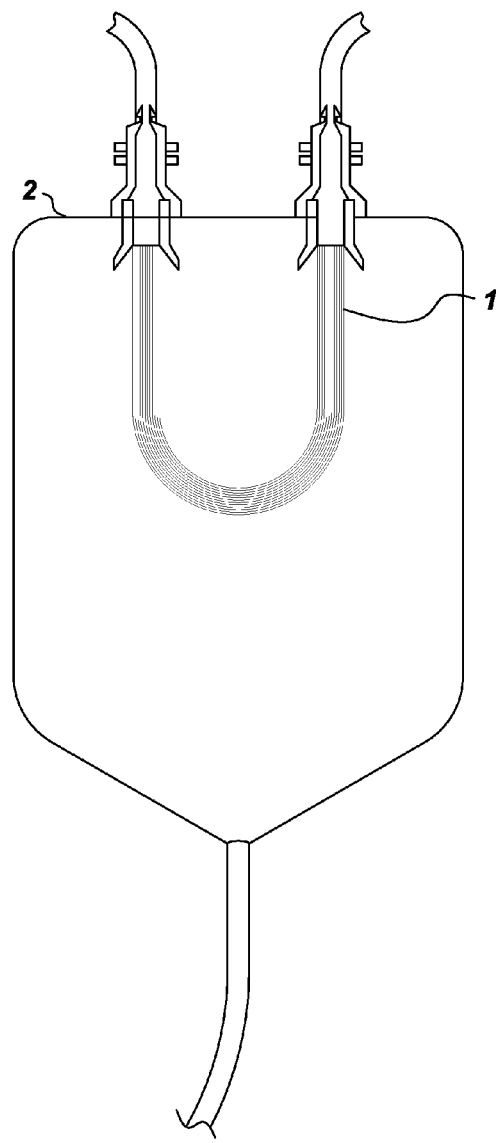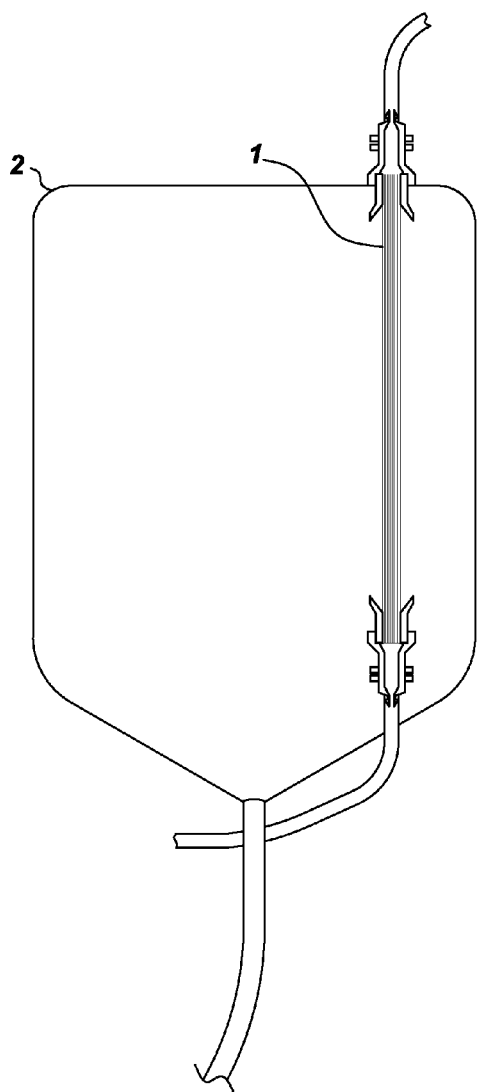
Fig. 1
Fig. 2

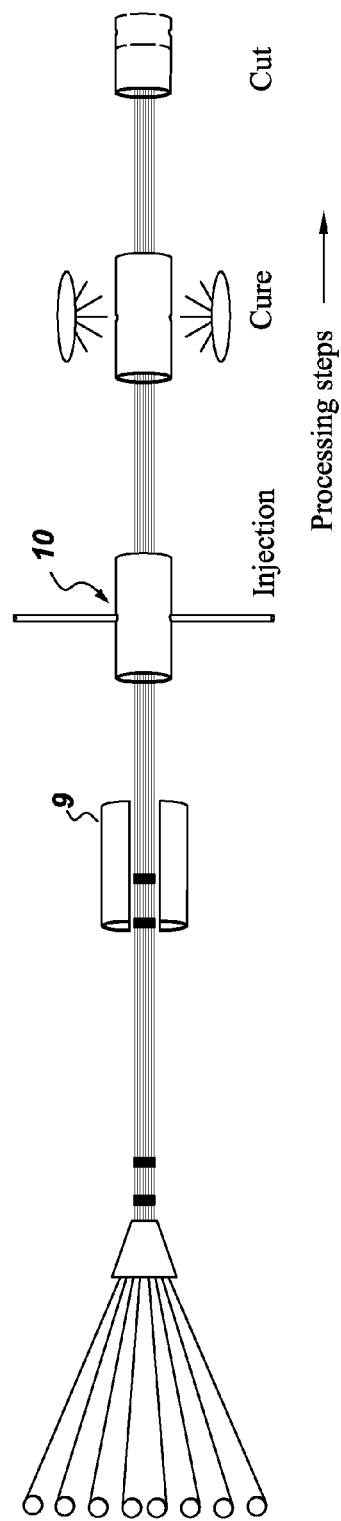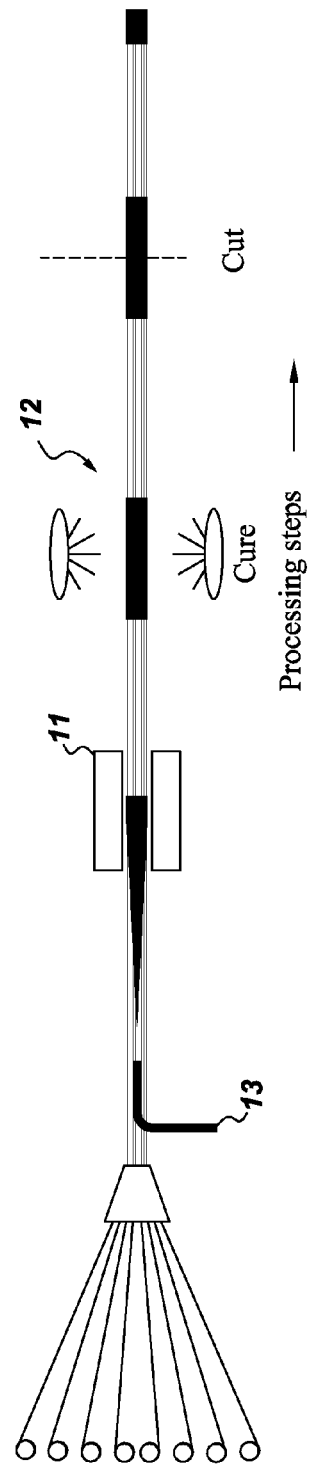

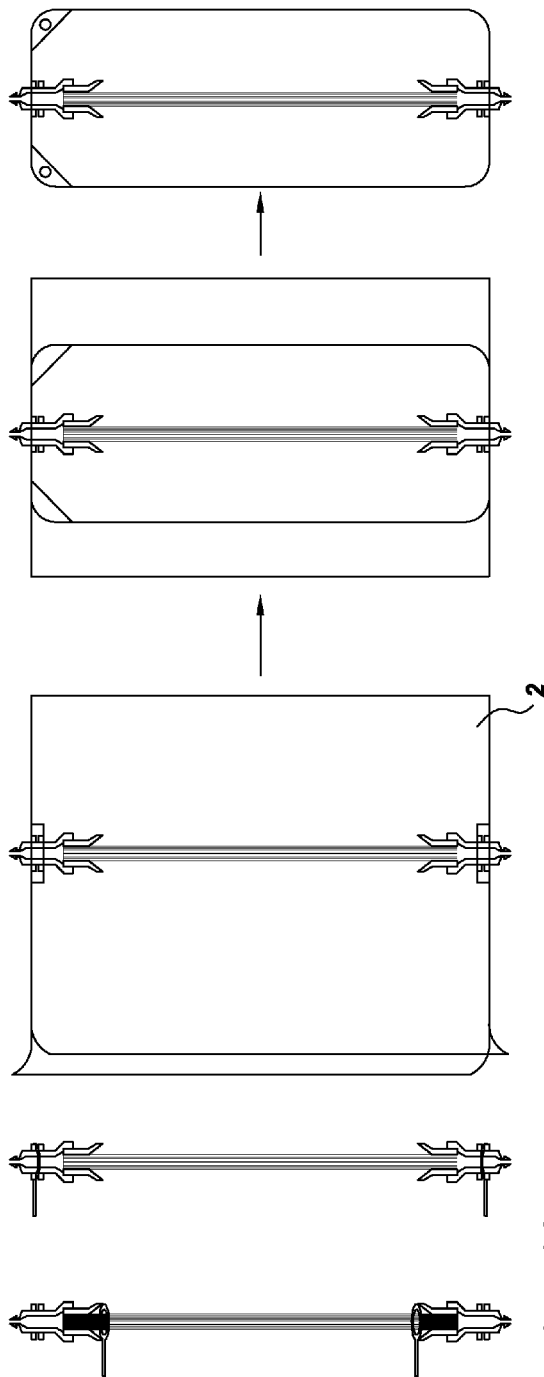
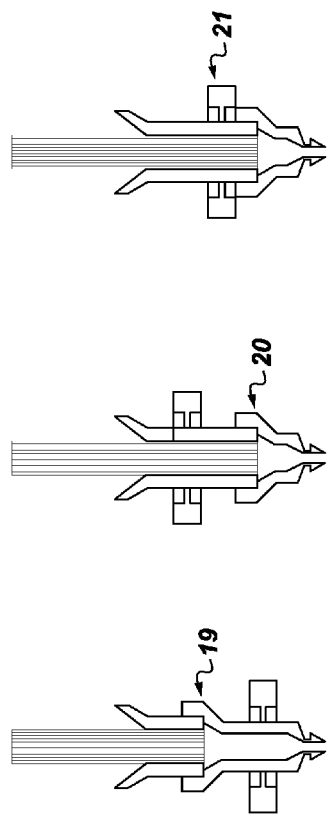
*Fig. 10*
*Fig. 11*

METHODS FOR MAKING A HOUSINGLESS HOLLOW FIBER FILTRATION APPARATUS

BACKGROUND

Hollow fiber filters are used extensively in pharmaceutical, health care, water filtration, gas filtration, and fluid sterilization applications. Typically, a hollow fiber filter is made using a maximum number of hollow fiber strands that will fit tightly and uniformly within a rigid cylindrical housing. The cylindrical housing is used to protect the hollow fibers themselves, which may be delicate and susceptible to damage.

In most hollow fiber filtration processes, the desired product is the permeate, which refers to material that passes through the membrane wall. For example, in the pharmaceutical industry, target proteins are removed from the cell culture through hollow fiber filtration; where the small proteins pass through the filter pores while the much larger cells are excluded. As such, hollow fiber filters are typically designed to allow for maximized recovery of the permeate, through washing or rinsing, as well as ease of scale-up to larger, commercial systems.

Currently, there is little difference in filter design between a large filter intended for thousands of hours of service in a pharmaceutical manufacturing plant and a small lab-scale filter intended for a short service lifetime.

Thus there is a need for design simplification and cost control that will expand the use of the filter in applications where cost or design complexities are concerns.

BRIEF DESCRIPTION

In general, the invention provides methods of manufacturing a housingless filtration apparatus. Methods include batch, continuous, and semi-continuous processes.

In one embodiment, a method of manufacturing a housingless hollow fiber filtration apparatus is provided comprising the steps of preparing a hollow fiber bundle and inserting the ends of the bundle into potting cups that contain a curable potting material, curing the potting material and cutting to expose the hollow fibers and retaining a portion of the potting cup, inserting end caps, arranging the end caps between two thermoplastic layers, and melt sealing the layers to form a container around the hollow fibers.

In one embodiment, a method of manufacturing a housingless hollow fiber filtration apparatus is provided comprising the steps of forming a continuous bundle of hollow fibers aligned longitudinally along a winding apparatus, applying a potting materials to the fibers to form a potting sleeve, cutting the bundle to expose the hollow fibers, attaching end caps, arranging the end caps between two thermoplastic layers, and melt sealing the layers to form a container around the hollow fibers.

In another embodiment, a method of manufacturing a housingless hollow fiber filtration apparatus is provided comprising the steps of forming a continuous bundle of hollow fibers aligned longitudinally along a winding apparatus, attaching end cap housings to the bundle of hollow fibers at a set position along the winding apparatus wherein the end cap housing comprises an exterior fill port, injecting a potting material into the exterior fill port and curing the material to form a potting sleeve around the fiber bundle, cutting the bundle to expose the hollow fibers, arranging the end caps between two thermoplastic layers, and melt sealing the layers to form a container around the hollow fibers.

Methods to increase rigidity of the using rigid films or additional perimeter compartments are also provided.

DRAWINGS

These and other features, aspects, and advantages of the present invention will become better understood when the following detailed description is read with reference to the accompanying drawings in which like characters represent like parts throughout the drawings, wherein:

FIG. 1 is a schematic drawing of an embodiment of the system of the invention where hollow fibers are directly laminated into a permeate bag part of a Cell Sample Processor (CSP) system.

FIG. 2 is a schematic drawing of the housingless filter in a vertical configuration

FIG. 6 is a schematic drawing of one embodiment showing a semi-continuous manufacturing process.

FIG. 7 is a schematic drawing showing a potting material being applied to the fiber bundle using an intermittent inkjet type spray nozzle in a continuous manufacturing process.

FIG. 10 is a process configuration for continuous sealing of hollow fibers within a flexible bag.

FIG. 11 is an illustration of various bag-sealing concepts.

DETAILED DESCRIPTION

Figure 3:
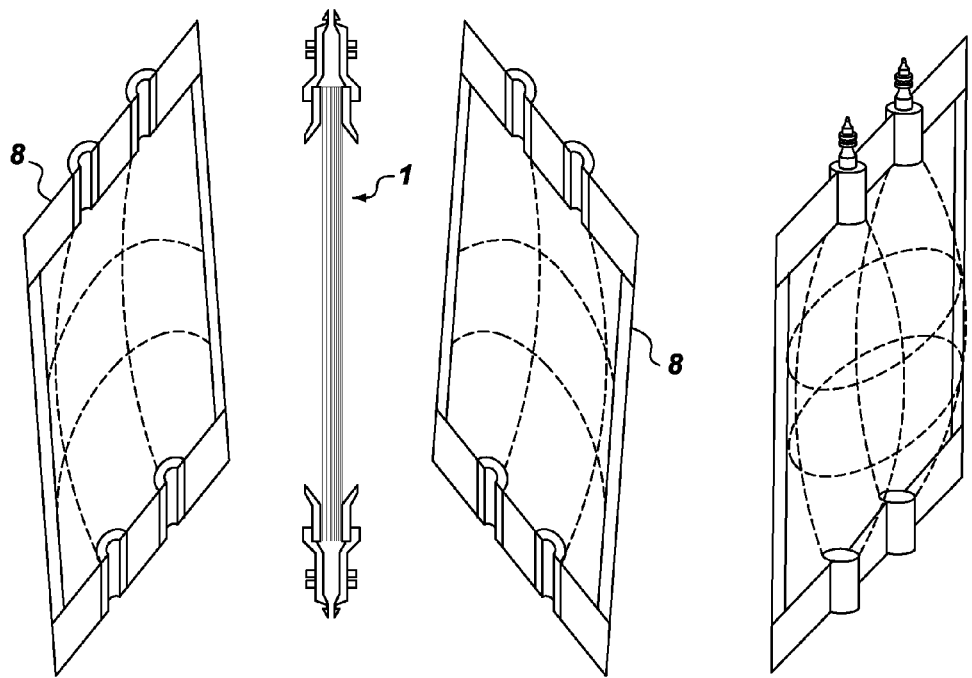
FIG. 3 is a schematic drawing of rigid thermoplastic parts used to form a three dimensional container around the hollow fibers.

In general, the invention described herein involves hollow fiber filtration apparatus designed to reduce component and manufacturing cost. Instead of a hollow fiber unit wherein the fibers are sealed in a separate cylindrical housing for support or protection, the hollow fibers are sealed directly into a flexible bag or rigid container that is an integral part of a filtration system. The flexible bag or rigid container may be used as a receptacle for a starting material, permeate, waste filtrate, or target retentate. Target retentate refers to one or more of submaterials that is intended to be separated from the starting material and collected separately.

In certain embodiments, a hollow fiber filtration unit is disposed directly in a flexible bag wherein the flow inlet and outlet to the inner lumen of the hollow fibers are capped with a flow port that extends outside of the bag. The apparatus design may reduce materials costs because the housing and permeate ports are eliminated. In addition, the housingless or bag filter design may allow for a reduction in number or size of other non-filtration components of a disposable filter set such as auxiliary tubing, fittings, and housing components. The design may also allow for a simplified manufacturing scheme.

One embodiment of the invention is shown in FIG. 1 wherein a housingless filtration unit may be designed such that the filtration unit is disposed within a unit of a filtration device which is used to separate or store filtered materials. As shown, the filter 1 is in a "U" shape, where the inlet and outlet to the filter are potted on the same side of a flexible bag 2. As illustrated the flexible bag may be used as a permeate collection bag in of a Cell Sample Processor (CSP) system wherein the housingless filter is disposed within the bag. While this invention may be used in a CSP system, it may also be used more generally in applications employing a hollow fiber filtration system. A filter with this configuration may function equivalently to a standard design, wherein the filter would be housed separately, but would not require the use of the filter housing and two permeate ports, significantly reducing filter material costs. Since, during filtration, positive pressure is located on the inner lumen of the fibers there should not be any implications from the use of a bag instead of a housing.

The configuration of the fibers within the bag may affect fluid handling and a configuration selected to meet process requirements that may depend on a wetted or non-wetted fiber exterior. In certain embodiments, the filter unit 1 may also be potted on opposite sides of the bag 2, as shown in FIG. 2. Such a straight-through configuration may give certain advantages, such as ease of pre-wetting the filter.

In certain embodiments an outside-in flow may be used and the filtration unit positioned accordingly. For example if the starting material is a biological material such as blood, the bag containing the filtration unit may be a blood bag. Suction could be used to purify the contained blood and leave waste in the blood bag (i.e., utilizing outside-in flow). In this case, one could place fibers across the bottom of the blood bag so they are continuously immersed in liquid, and the system can use a back flush to clean off fibers. This may be of use in cases where it is desired to pre-filter an incoming material that may be high fouling or too viscous to push through the inner lumens.

A possible disadvantage of using a bag filter in certain applications may be the back-seepage of permeate if there is no active forward flow through filter. This may be avoided with the proper bag filter design. For example, in certain embodiments the hollow fibers may be isolated from the permeate pool in the bag through the use of a U-shape configuration or by potting horizontally at top of bag so the fibers are not immersed in permeate.

In certain embodiments, the containers may be cut or sized to conform to a specific process so as not to be constrained to a linear cylindrical geometry as a standard hollow fiber filter is. In certain embodiments, the container may comprise planar flexible films that were melt sealed to form a flexible bag cavity. In other embodiments, the flexible bag may have a three dimensional shape, such as a blow-molded bag. The bag may also contain multiple inlet and outlet ports in addition to those used with the hollow fiber filtration unit.

In certain embodiments, a hollow fiber filtration unit 1 may be disposed in a rigid container where the container has a pre-formed three-dimensional shape. In certain embodiments the container is formed from melt sealing two separate thermoplastic parts 8 such as, but not limited to, an injection molded, compression molded, or blow molded part. During production, the filter components and additional fitments are placed in the proper areas on one of the rigid parts. A second the second rigid part is arranged on top and melt-sealed to the filter and fitment components and the first rigid part to form a sealed container. The rigid walls of the container may impart more protection for the hollow fibers than compared to a flexible bag filter. A representative embodiment of a rigid container is shown in FIG. 3.

The filter may be designed to retain flexibility, even during use. This feature may be advantageous in applications where space is constrained, such as a military field first aid kits. In other applications it may be desirable to protect the housingless filter from the possibility of fiber damage. In certain applications fixing the filter-in-a-bag within a packing tray may be desirable. The packing tray may be a rigid or a semi-rigid design. In other applications, a reinforced hollow fiber may be used.

Figure 4:
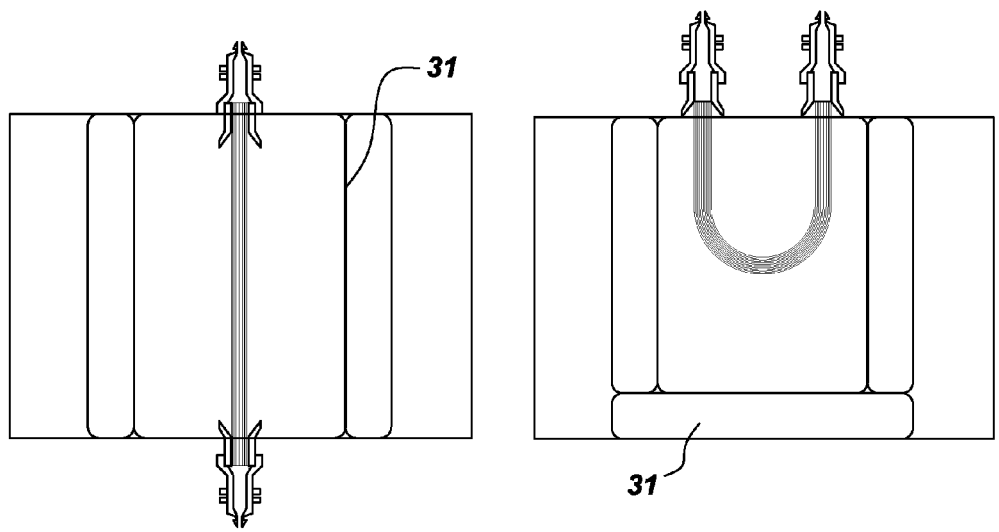
FIG. 4 is a schematic drawing showing the use of three dimensional compartments for added rigidity.

An initially flexible bag filter may be designed to be rigid to protect the hollow fibers from damage during shipping and use. This may be accomplished by creating additional chambers within the bag that are filled with air during production and sealed. In alternative embodiments, other gases, liquid, or foam may be used to fill the compartments. This imparts rigidity to the filter system without the use of additional components and may provide a lower cost solution than a system requiring an additional protective structure. As shown in FIG. 4 in certain embodiments, the additional chambers are formed in the production process by providing additional melt seals 31 longitudinally along opposing sides of the flexible films that may be used to form a flexible bag. The melt seals create two additional compartments along the peripheral edges of said flexible bag.

As shown further in FIG. 4, a similar process may be used when the inlet and outlet ports are in juxtaposition along one edge of the flexible bag The two planar flexible films which are used to form the bag may be melt sealed 31 along the opposing side of the inlet and outlet ports to form a compartment along the lower edge of the flexible bag which may also be filled with gas, liquid, or foam to provide support.

In certain embodiments the components of the hollow fiber filter apparatus polymeric comprised material that can be sterilized and which meets at least one of FDA and USP requirements for biocompatibility. This includes materials used in construction of the hollow fiber bundles, potting material, end caps, and the flexible bag. Also included may be auxiliary components such as retention clips, sealants, and adhesives, which may come in contact with the materials undergoing filtration or processing.

The hollow fiber filter apparatus may be produced using a variety of manufacturing methods. The manufacturing methods may include a batch, semi-continuous, or a continuous process.

Figure 5:
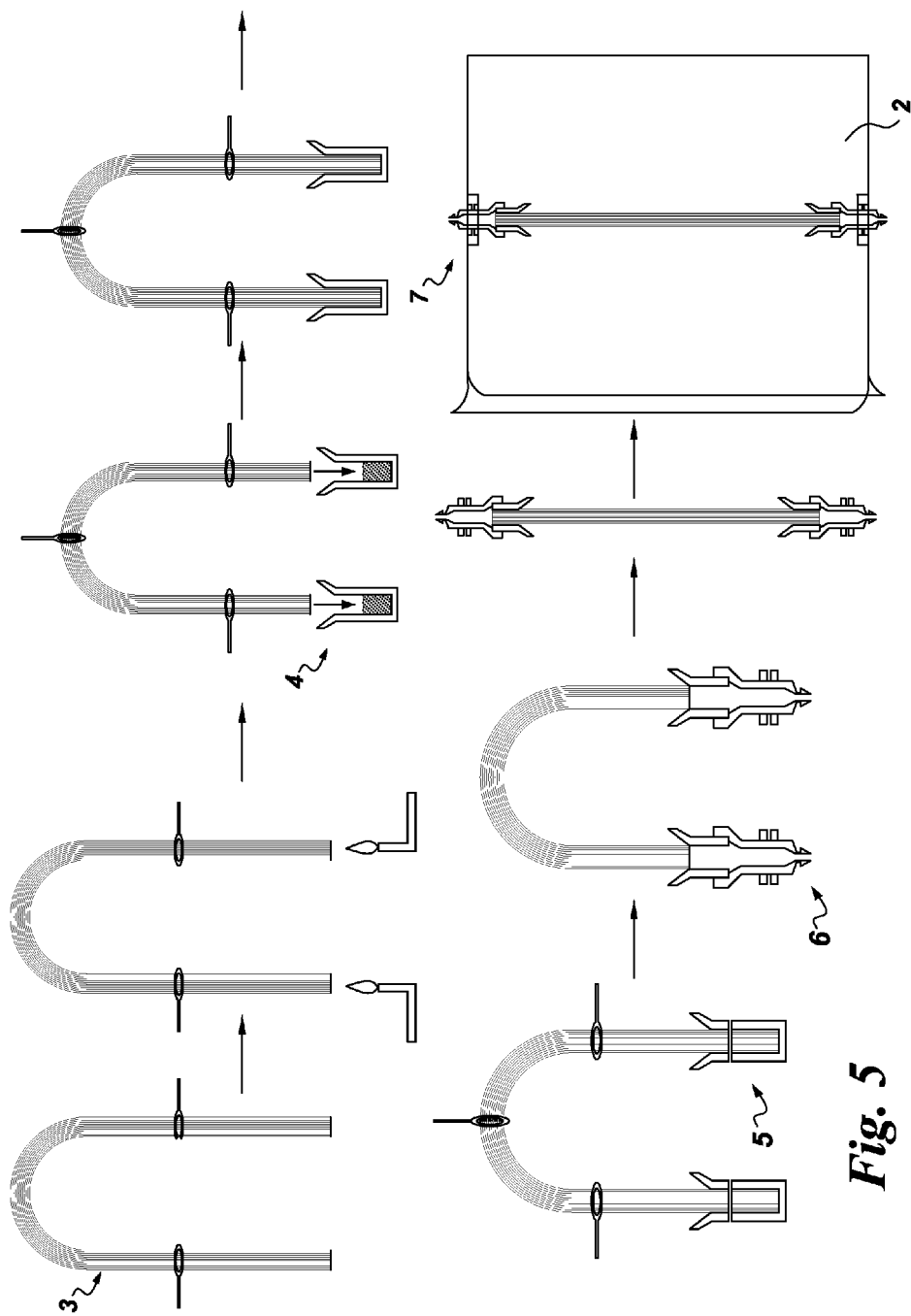
FIG. 5 is a schematic drawing of one embodiment showing a batch process used to construct the hollow fiber unit.

FIG. 5 is a schematic drawing of one embodiment showing a batch process, which may be used to construct the hollow fiber unit, which may then be disposed within a flexible bag. As shown, a bundle of hollow fibers 3 is sized to fit within a desired apparatus and a blocking step performed. The blocking step may be one of several methods: thermal (laser, heat gun, flame, hot wax, hot knife, etc.) or chemical (UV or heat curable epoxy, polyurethane, silicone, acrylic resin, etc) whereby the ends of the hollow fiber bundle have a relatively smooth cross-sectional surface. Two potting cups 4 may be filled with a potting material and the two ends of the hollow fiber bundle inserted into each. The potting material is a curable adhesive that is used, in part to form a seal around the hollow fiber bundle and provide adhesion. The potting material may comprise a UV cured adhesive, visible light cured adhesive, heat cured adhesive, thermoplastic resin, thermoset resin, or combination thereof. In certain embodiments the potting material may be a UV or heat curable epoxy, silicone, polyurethane, or an acrylic resin it.

The design of potting cups may be non-cylindrical. The non-cylindrical design, such as a tapered top, may allow for a single fiber insertion step, without overflowing of uncured potting material. Over time, the potting material may settle into the inter-fiber space, providing a good seal. The potting cups may be configured to allow for rapid immersion of the fiber bundle while limiting the amount of overflow of material out of the cups, and limiting the length of fiber that is exposed to the potting material.

As shown further in FIG. 5, a cross-sectional cut is made through the proximal ends of each potting cup to from a potting sleeve 5 and exposing open hollow fibers. Thus the potting sleeve is comprised of the potting material. The cross-sectional cut may be made before, during, or after curing of the potting material. An end cap 6 may then be inserted over each potting sleeve. The end caps may be of various designs to allow insertion into the inlet and outlet ports 7 of the flexible bag 2.

FIG. 6 is a schematic drawing of one embodiment showing a semi-continuous manufacturing process wherein a continuous bundle of hollow fibers is aligned longitudinally along a winding apparatus. As shown the end cap housings 9 may be attached to the bundle of hollow fibers at set positions along the manufacturing process. The position may be chosen based on the desired filtration unit size. The end cap housing may be comprised of two parts that are fitted together in a clamshell type arrangement and also comprise an exterior fill port 10. A potting material may be injected into the exterior fill port such that potting material contacts the underlying bundle of hollow fibers. The potting material is then cured to form a potting sleeve. The end cap housing may be cut in a cross sectional fashion to expose open hollow fibers while retaining a portion of the end cap housings. More than one cut may be used to remove the fill port.

The end caps may attached to the potting sleeve through a variety of methods including, but not limited to adhesive, solvent bond, threaded seal, retaining clip, melt seal, pressure fit, or a combination thereof.

In an alternative embodiment, the functionality of the potting sleeve and end cap may be combined into a single unit having the functionality of providing adhesion to the fiber bundles and a point of attachment to the flexible bag.

The bag may be constructed over the hollow fiber unit. As shown, the hollow fiber unit may be positioned between two flexible sheet films and the peripheral edges of the two planar flexible films are sealed together to form the flexible bag. In certain embodiments, the positioning of the hollow fiber unit is aided by providing two film layers where the film layers have matching apertures along the edges of the films to form inlet and outlet ports when sealed. The hollow fiber unit may be positioned between the two flexible sheet films such that the end cap housings are inserted into the apertures. The peripheral edges of the two planar flexible films may be sealed to form a flexible bag. In an alternative embodiment, rigid three-dimensional parts may be used in place of the flexible films to provide a rigid container for the hollow fibers.

In other embodiments, the hollow fiber unit may be disposed separately within a pre-formed container and the end caps may then be inserted into the inlet and outlet ports of the container. The hollow fiber unit may be disposed within the container prior to sealing. In other embodiments, the hollow fiber unit may be inserted through the inlet or outlet port into the container. In each embodiment the container may be a flexible bag or a rigid container and results in a closed filtration apparatus.

FIG. 7 shown an embodiment using a continuous manufacturing process whereby a potting material is applied to a bundle of hollow fibers at a set position along the winding apparatus. As shown in FIG. 7, a UV curable potting material 11 is applied using an intermittent inkjet type spray nozzle. Alternative methods of applying the potting material directly to the fiber bundle may also be used including, but not limited to spray coating, roll coating, and blade coating. The potting material is cured on line to form a potting sleeve 12. The hollow fibers may then be cut along the potting sleeve to expose open hollow fibers while retaining a portion of the potting sleeves. End cap housings may be attached to the end portions of the potting sleeve to form the hollow fiber unit. In other embodiments, the potting sleeve may act as an end cap housing and be inserted directly into the inlet and outlet ports of the bag.

As shown further in FIG. 7, in certain embodiments a nozzle 13 may be positioned within the hollow fiber bundle infusing a sealant coating on to an interior section. The sealant coating may provide adhesion between the fibers. The sealant may be the same as or a different material than the potting material. In certain embodiments the potting material may be used however processing aids or solvents may be added to alter the viscosity or other properties to aid in dispersion.

In certain embodiments fibers may be added at various times during the inline winding process to increase the size of the fiber bundle while maintaining bundle integrity or strength. The sealant coating may also be added at different times during the manufacturing process, upstream or downstream of the potting material.

Figure 8:
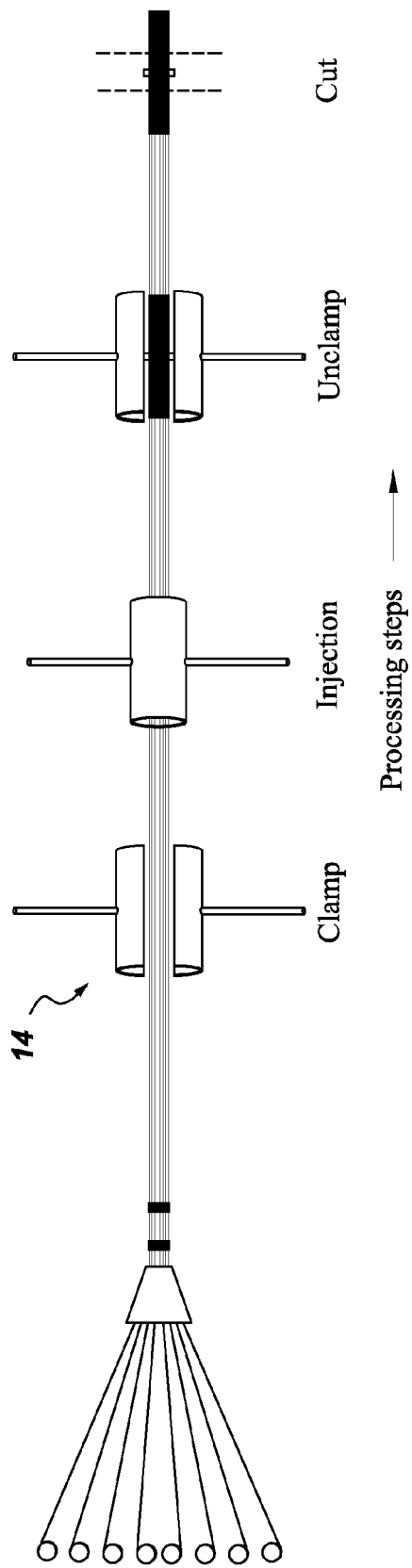
FIG. 8 is a schematic drawing showing potting material being applied using a hot resin fill with a retractable mold.

FIG. 8 is a schematic drawing of an embodiment showing potting material being applied as a hot thermoplastic resin fill with a retractable mold 14. An advantage of this process is that the mold will provide a good cylindrical shape for mating with the end cap. An injectable resin may be selected as the potting material that has a mold-filling rate sufficient to seal the fibers, without causing the fibers to collapse or melt. The material should also have good mold release properties The injectable resins may include, but is not limited to, high flow polypropylene or ethylene vinyl acetate.

Figure 9:
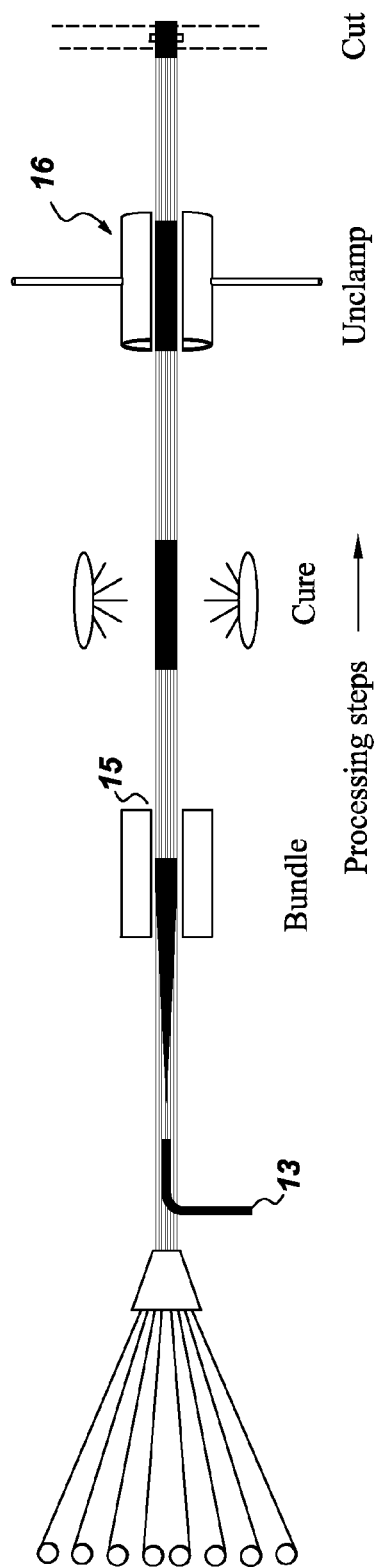
FIG. 9 is a schematic drawing showing a combination curable compound and hot melt seal process.
Figure 12:
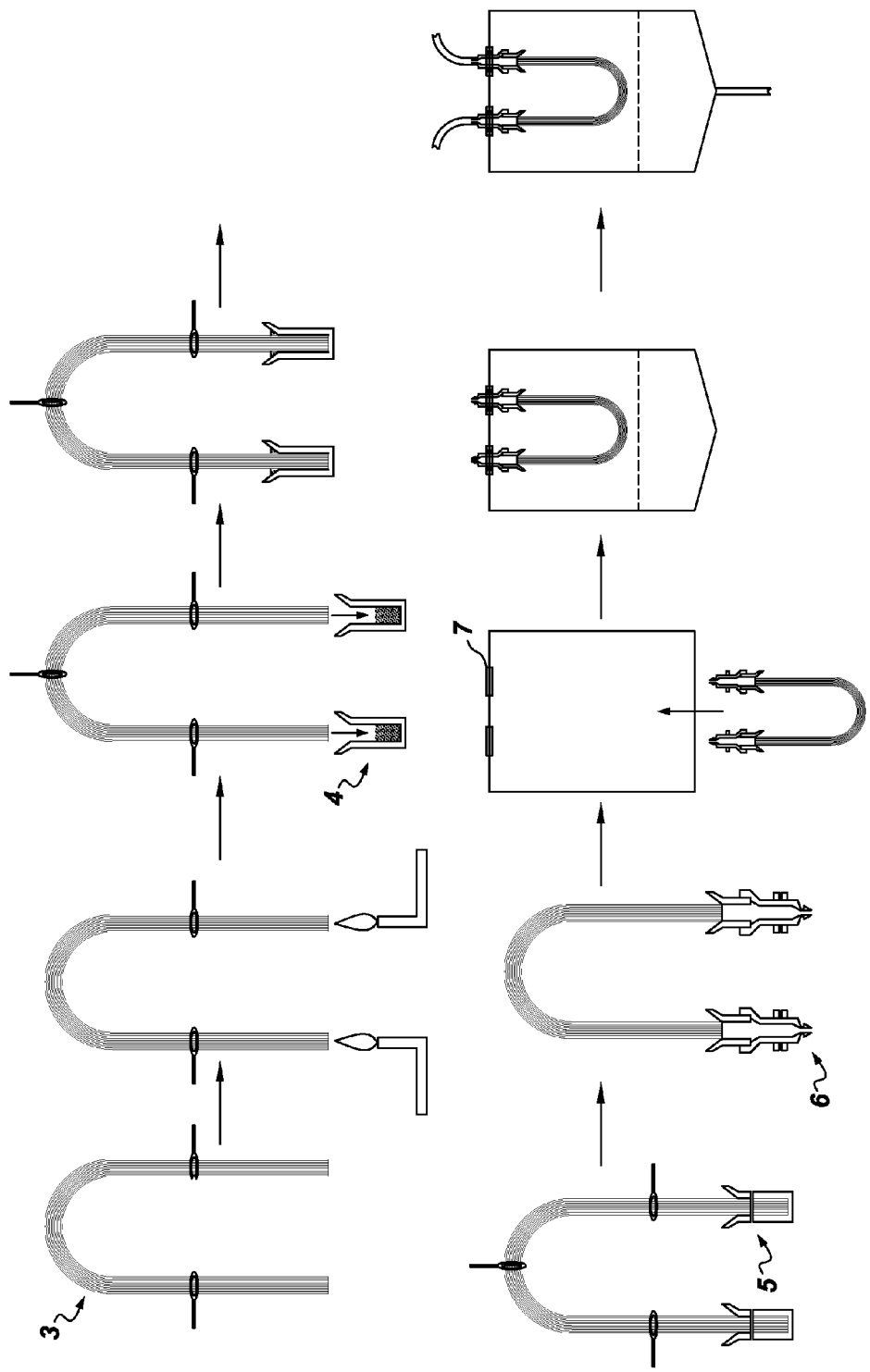
FIG. 12 is a schematic drawing of an assembly scheme for a U-shape filter.

Other embodiments may combine both spray coating and in-line molding to form the hollow fiber unit. This is shown in FIG. 9 where a UV cure resin on the interior and exterior of the fiber bundle 15 is used followed by an injection over molding of hot thermoplastic resin 16. The over molding may be used to insure dimensional specification related to shape and outer diameter of the potting sleeve and allow adequate mating with an end cap while the initial UV spray coating may give sufficient rigidity to maintain the integrity of the hollow fiber lumens during the molding step.

In certain embodiments, the hollow fiber unit may be disposed within a preformed flexible bag and the end caps attached to the inlet and outlet port of the flexible bag. The attachment of the end cap to the bag may use a variety of methods including, but not limited to a solvent bond, threaded seal, melt seal, or a combination thereof.

FIG. 10 shows one embodiment of the process by which a hollow fiber unit 1 is sealed in the bag 2. The process may use a clamshell type press wherein rapidly cooled platens may be used to seal the fibers in bag.

Alternative bag sealing concepts are shown in FIG. 11 and depict various sealing techniques of the hollow fiber bundles. As shown, the bundles may be adhered using an end cap melt seal 19, a seal directly to the end caps, a housing melt seal 20, or a combined melt seal 21 method which may be used in certain embodiments. An end cap melt seal may be used to maintain sterility if there is a rupture in the filter unit. The end cap melt seal would insure the material is contained in the bag, allowing for full sterile recovery and testing in a different filter set. A combined hybrid melt seal would also maintain sterility as well as eliminating the need for a solvent weld or threaded connection. In each embodiment, a rigid thermoplastic part may be used in place of the bag.

Experimental

A housingless filter was constructed using the batch process illustrated in FIG. As shown, a hollow fiber bundle 3 is blocked, inserted into potting cups 4 containing potting material and a potting sleeve 5 is formed around the bundle. End caps 6 are attached and inserted into inlet and outlet ports 7 of the filter bag. The filter was tested in a paired test with a standard housing type filter. Results are shown in Table 1.

TABLE 1

Results of paired test of standard and housingless U-shape filters

|  | Standard filter | Filter in a bag |
| --- | --- | --- |
| TNC/MNC | 75.8% ± 1.8% | 76.1% ± 1.8% |
| recovery | 65.7% ± 3.6% | 67.2% ± 2.4% |
| Final hematocrit | 10.7% ± 0.1% | 7.9% ± 0.1% |
| Final volume | 21.7 mL | 24.1 mL |

As shown in Table 1, the cell recoveries with a housingless filter apparatus are essentially the same as the control; small difference may be attributed unrelated process variables. TNC refers to total nucleated cells; MNC refers to mono nucleated cells. During filtration, no significant operational issues were observed with the housingless filter. A slightly elevated feed pressure for the housingless filter was noted along with a slightly lower filtration time. Both of these effects are most likely due to having a slightly larger fiber length in the housingless filter as compared with the control.

Figure 13:
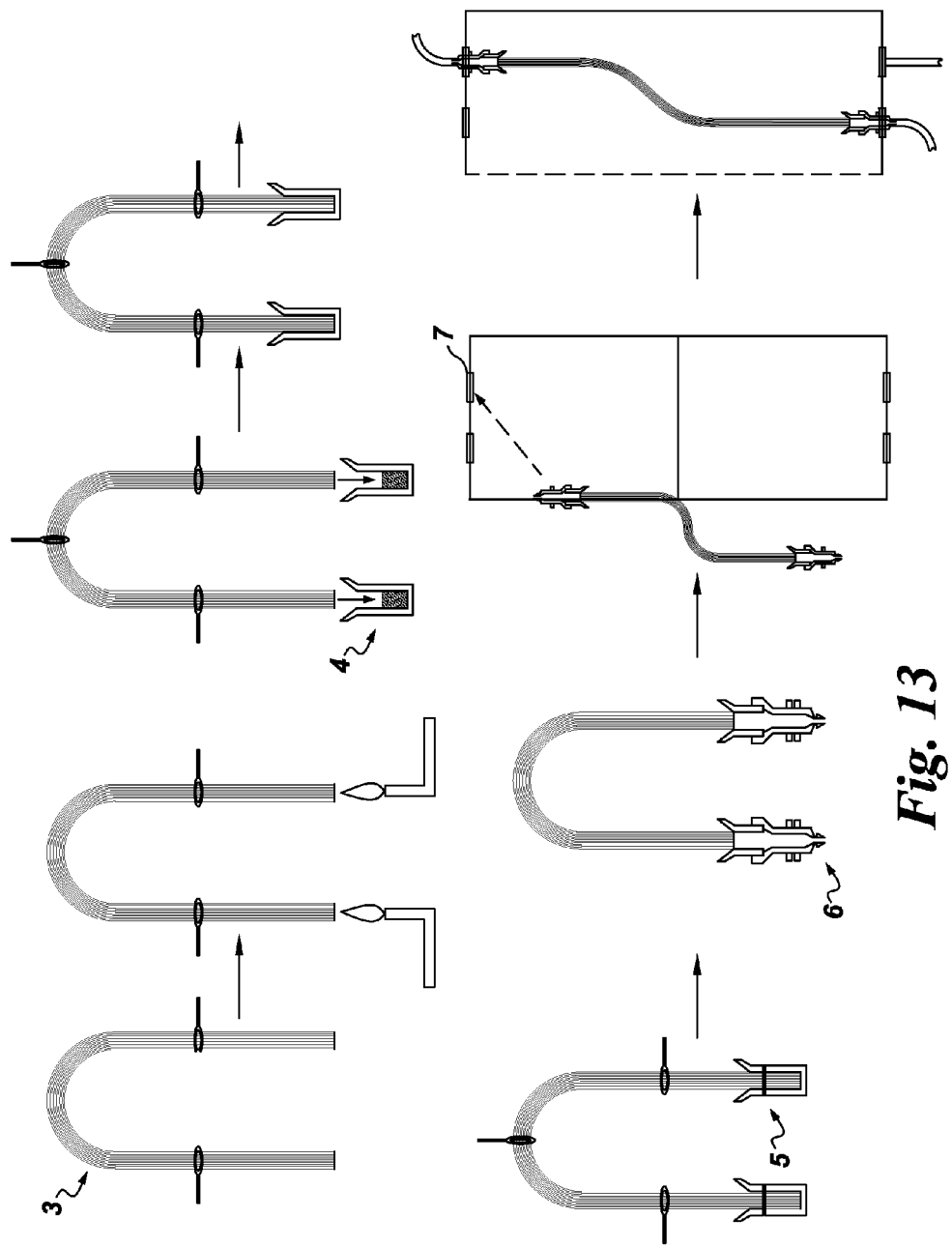
FIG. 13 is a schematic drawing of an assembly scheme for a straight through filter.

A second bag filter was constructed according to the process shown in FIG. 13. A thermal block of fibers was used. The bag filter was also made in a "straight-through" configuration to help with fiber wetting. The fluid flow path during the filtration step was from the top down. Table 2 shows the result of the flow through filter compared to a control.

TABLE 2

Results of paired test of standard and housingless filters straight configuration

|  | Standard filter | Filter in bag |
| --- | --- | --- |
| TNC/MNC | 89.3% ± 4.0% | 90.8% ± 4.1% |
| recovery | 88.6% ± 3.0% | 91.5% ± 3.2% |
| TNC viability | 98.3% ± 0.1% | 98.6% ± 0.3% |
| Final hematocrit | 32% ± 0.1% | 31.4% ± 0.1% |
| Hemolysis | 0.8% ± 0.01% | 0.6% ± 0.01% |
| Final volume | 21.2 mL | 22.2 mL |

Figure 14:
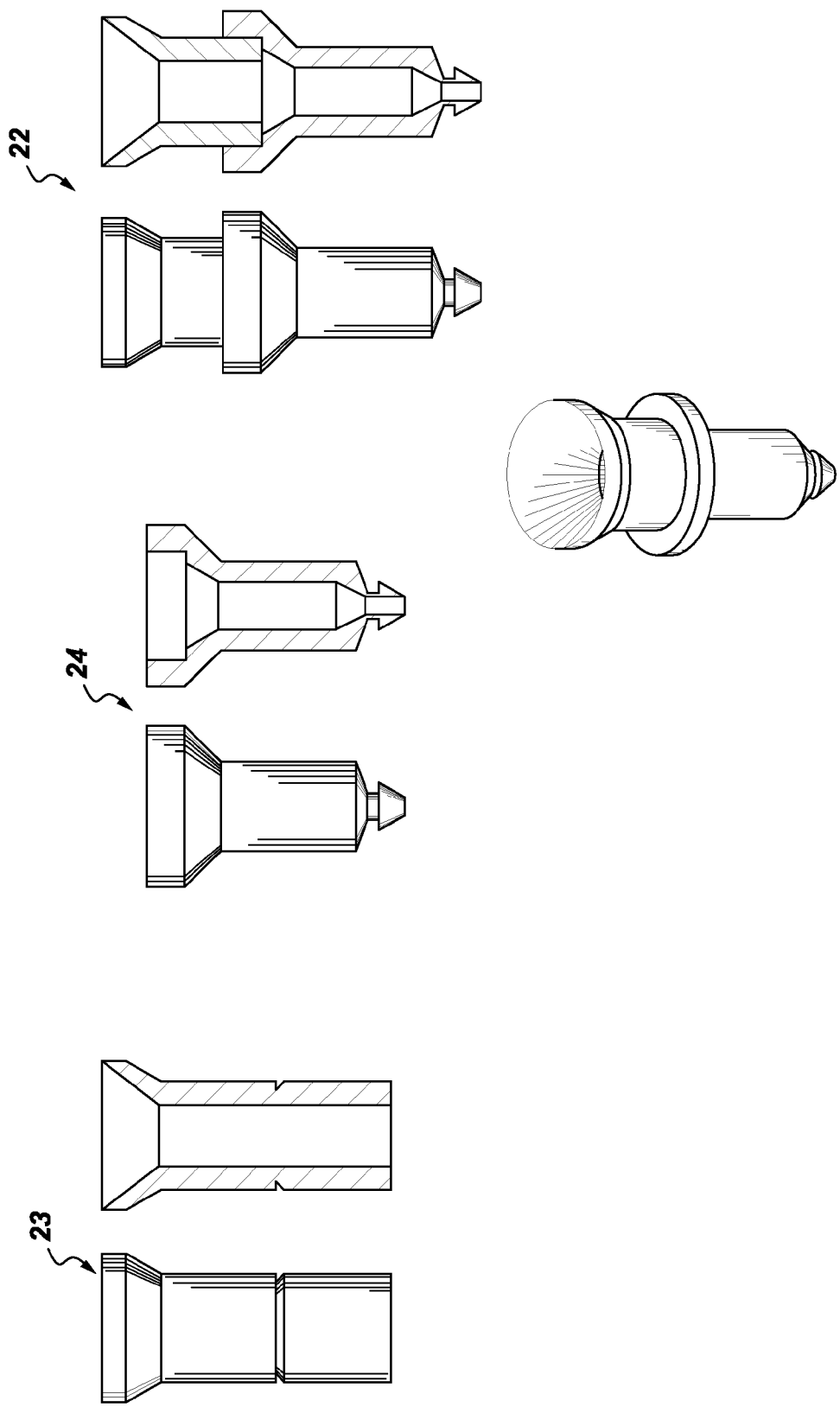
FIG. 14 is a schematic drawing of an end cap filter design.

A typical end cap design for manual potting operations and testing is shown in FIG. 14. The unit 22 is a combined breakable potting cup 23 with a bonded end cap 24 to allows for a manual potting step that does not require operator adjustment of potting cup height. The design of the potting cup is non-symmetrical having a closed cylindrical lower portion and an open funnel shaped upper portion to allow for a single fiber insertion step of the fiber bundle, without potting material overflowing or running up too high on the fibers. The ends cap housing has a tapered design such that the inner diameter of the end cap housing, on the side opposite the hollow fiber bundle, is reduced. The end cap design may reduce stagnation volume of material in this area of the filtration. The design may allow for air purge to more completely displace material present in the endcap.

Figure 15:
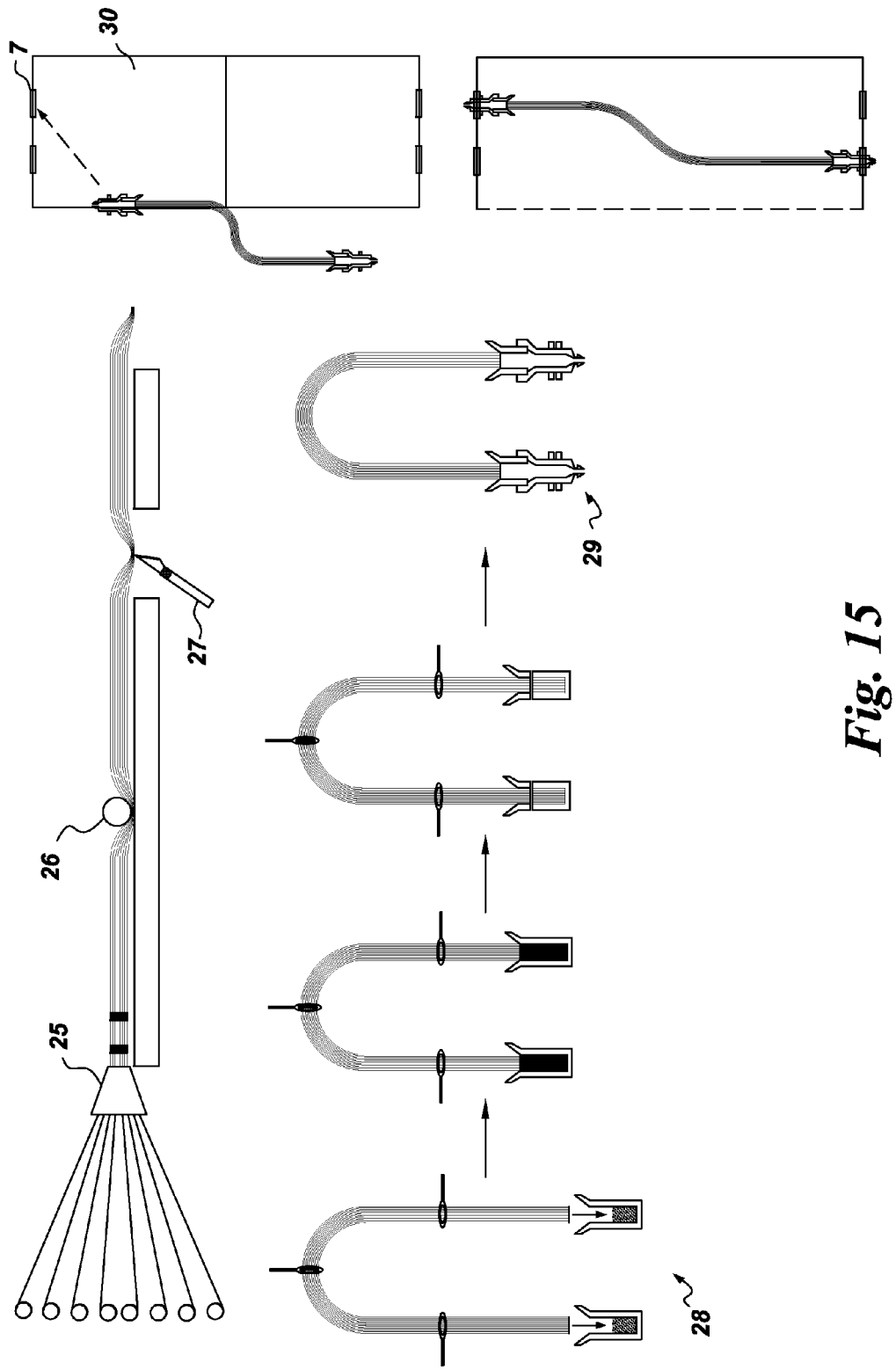
FIG. 15 is a schematic drawing of a process for attaching an end cap and insertion into a flexible bag.

A process for attaching the end caps is shown in FIG. 15. A total number of twenty-one fibers, were drawn into a bundle using a reducing device 25, in this case a funnel. At the desired length, the fiber bundle is crimped with a cylindrical metal bar 26 and tightly bundled using a thin piece of scotch tape. A hot knife 27 (Thermo-Schneider 20 ZTS, knife temp at approximately 400° F.) was used to cut the bundle. The cut can be made so that the fibers are melt sealed on both sides of the cut. The fiber bundle is then potted in the customized potting cup 28; the tight bundle provided by the scotch tape allows the fibers to be inserted easily into the cup.

Because the end of the fiber bundle is tightly held together from the melt seal, the standard potting epoxy of two parts EPON® Resin 828 (Shell Chemical Company) and one part Epi-cure® 3140 (Shell Chemical Company) is too viscous to fully penetrate the inter-fiber area before curing. We have found that mixing the standard epoxy, heating the mixture at 40° C. for 15 min, pouring into the potting cup, and inserting the fibers, and holding at 40° C. fully penetrates the inter-fiber area within the bundle and gives a good seal after 24 hr. After curing, the ends of the cup are broken off (a tab on the cup facilitates this step), and the end caps 29 are inserted. The end caps were sealed with a small amount of polysulfone glue (polysulfone chips dissolved in methylene chloride). The fiber assembly is inserted into a bag 30 by pushing the end caps through the bag ports and melt sealing the bag. In an alternative production laminating two EVA sheets around the end caps may be used to form a flexible bag.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method of manufacturing a hollow fiber filtration apparatus comprising the steps of:
    forming a continuous bundle of hollow fibers aligned longitudinally along a winding apparatus;
    attaching end cap housings to the continuous bundle of hollow fibers at a set position along the winding apparatus wherein the end cap housing comprises an exterior fill port;
    injecting a potting material into the exterior fill port such that potting material contacts the bundle of hollow fibers;
    curing the potting material to form a potting sleeve;
    cutting the end cap housings to expose open hollow fibers while retaining a portion of the end cap housings;
    providing two thermoplastic parts wherein said thermoplastic parts have matching apertures along the edges of the thermoplastic parts to form inlet and outlet ports when sealed;
    positioning the hollow fiber unit between the two thermoplastic parts such that the end cap housings are inserted into the apertures; and
    melt sealing the peripheral edges of the two thermoplastic parts together to form a closed filtration apparatus.

2. The method of claim 1 wherein the end cap housings are attached using a two part locking connection, overmolding, or a combination thereof.

3. The method of claim 1 wherein the potting material comprises a UV cured adhesive, visible light cured adhesive, heat cured adhesive, thermoplastic resin, thermoset resin, or combination thereof.

4. The method of claim 1 further comprising the step of applying a sealant coating to the bundle of hollow fibers to provide adhesion between fibers.

5. The method of claim 1 wherein the thermoplastic parts comprise planar flexible films.

6. The method of claim 5 further comprising the steps of:
   forming additional melt seals longitudinally along opposing sides of the planar flexible films to form a flexible bag having two additional compartments along the peripheral edges of said flexible bag; and
   filling said compartments with at least one of air, liquid, or foam.

7. The method of claim 6 wherein the inlet and outlet ports are in juxtaposition along one edge of the flexible bag and the planar flexible films are melt sealed along the opposing side of the inlet and outlet ports to form a compartment along the lower edge of the flexible bag and wherein said compartment if filled with at least one of air, liquid, or foam.

8. The method of claim 1 wherein the thermoplastic parts comprise rigid three-dimensional parts.

9. The method of claim 1 wherein the end cap housing is attached to the inlet port and outlet port by an adhesive, solvent bond, threaded seal, retaining clip, melt seal, compression seal, pressure fit, or a combination thereof.

10. The method of claim 1 further comprising the step of applying a sealant coating to the bundle of hollow fibers to provide adhesion between fibers.

* * * * *